United States Patent
Hauer et al.

(10) Patent No.: US 9,357,968 B2
(45) Date of Patent: Jun. 7, 2016

(54) SELF-CLEANING SENSOR SURFACES FOR IMPLANTABLE SENSOR SYSTEMS

(75) Inventors: Marc Hauer, Zurich (CH); Thomas Doerr, Berlin (DE)

(73) Assignee: DYCONEX AG, Bassersdorf (CH)

( * ) Notice: Subject to any disclaimer, the term of this patent is extended or adjusted under 35 U.S.C. 154(b) by 683 days.

(21) Appl. No.: 13/169,392

(22) Filed: Jun. 27, 2011

(65) Prior Publication Data

US 2012/0016220 A1  Jan. 19, 2012

Related U.S. Application Data

(60) Provisional application No. 61/364,029, filed on Jun. 14, 2010.

(51) Int. Cl.
*A61B 5/05*     (2006.01)
*A61B 5/00*     (2006.01)
*A61B 5/145*    (2006.01)

(52) U.S. Cl.
CPC ........... *A61B 5/6867* (2013.01); *A61B 5/14503* (2013.01); *A61B 2562/162* (2013.01); *A61B 2562/245* (2013.01)

(58) Field of Classification Search
CPC ............. A61B 5/4266; A61B 5/14532; A61B 5/0408; A61B 5/145; A61B 5/0422; A61B 18/1492; A61B 5/6867; A61B 5/14503; A61B 2562/245; A61B 2562/162; A61N 1/0556
USPC ......... 600/346, 347, 364, 365, 381, 377, 373, 600/372, 395
See application file for complete search history.

(56) References Cited

U.S. PATENT DOCUMENTS

| | | | | |
|---|---|---|---|---|
| 5,062,841 A * | 11/1991 | Siegel | | 604/891.1 |
| 5,387,327 A * | 2/1995 | Khan | | 600/347 |
| 6,019,877 A * | 2/2000 | Dupelle et al. | | 204/196.11 |
| 6,477,395 B2 * | 11/2002 | Schulman | | A61B 5/14865 600/345 |
| 7,241,477 B2 * | 7/2007 | Chang et al. | | 427/398.4 |
| 2001/0037099 A1 * | 11/2001 | Effenhauser | | 604/352 |
| 2003/0114735 A1 * | 6/2003 | Silver et al. | | 600/300 |
| 2005/0096587 A1 | 5/2005 | Santini, Jr. et al. | | |
| 2006/0257996 A1 | 11/2006 | Simpson et al. | | |
| 2007/0265692 A1 * | 11/2007 | Koop et al. | | 607/119 |
| 2007/0281353 A1 * | 12/2007 | Vacanti et al. | | 435/367 |
| 2008/0033260 A1 * | 2/2008 | Sheppard et al. | | 600/301 |
| 2008/0082162 A1 * | 4/2008 | Boismier et al. | | 623/1.38 |
| 2009/0198117 A1 * | 8/2009 | Cooper et al. | | 600/347 |
| 2010/0144007 A1 * | 6/2010 | Bryant et al. | | 435/182 |
| 2010/0145286 A1 * | 6/2010 | Zhang | | A61L 17/005 604/265 |
| 2010/0185037 A1 * | 7/2010 | Uhland et al. | | 588/302 |

OTHER PUBLICATIONS

European Search Report and Notes for the European Search Report on the European Patent Application No. EP 11 17 2370, dated Aug. 25, 2014 (8 pages).

* cited by examiner

*Primary Examiner* — Michael Kahelin
*Assistant Examiner* — Tho Tran
(74) *Attorney, Agent, or Firm* — Buchanan Ingersoll & Rooney PC

(57) ABSTRACT

Implantable sensor system including a sensor which is situated in a housing, the housing having a measurement region which is permeable for the parameters to be detected by the sensor, wherein the measurement region has an erodible protective coating which is permeable for the parameters to be detected by the sensor.

15 Claims, 3 Drawing Sheets

SELF-CLEANING SENSOR SURFACES FOR IMPLANTABLE SENSOR SYSTEMS

CROSS-REFERENCE TO RELATED APPLICATIONS

This patent application claims the benefit of co-pending U.S. Provisional Patent Application No. 61/364,029, filed on Jul. 14, 2010, which is hereby incorporated by reference in its entirety.

TECHNICAL FIELD

Implantable sensor systems are known, and are used in the medical field, for example, to detect certain medically relevant parameters in the human body. Such sensor systems are usually used to detect parameters in body fluids over a given period of time. For this purpose, the sensor systems are implanted in such a way that the sensor system is in functional contact with the body fluid having the parameter to be measured, so that the sensor is able to detect the parameter to be measured. The present invention is directed toward providing an alternative approach to delay or prevent premature encapsulation of an implanted sensor system.

BACKGROUND

One problem with implanted sensor systems is that, within a certain time after implantation in the body, they are recognized as foreign bodies and encapsulated, and are thus decoupled from the body fluids. As a result of this decoupling, the functional contact between the body fluid and the sensor system is adversely affected, and may even be interrupted.

The first step in the encapsulation generally consists of the agglomeration of autologous material at the surface of the implanted sensor system. On the basis of the agglomeration of autologous material which has occurred, this is followed by overgrowth and inclusion of the sensor system by connective tissue cells (see James M. Anderson, Analiz Rodriguez, and David T. Chang: Foreign body reaction to biomaterials; http://www.sciencedirect.com/science?_ob=ArticleURL&_udi=B6WX3-4RFD6BC-1&_user=7184476&_coverDate=04%2F30%2F2008&_rdoc=1&_fmt=high&_orig=search&_sort=d&_docanchor=&view=c&_searchStrId=1357446928&_rerunOrigin=scholar.google&_acct=C000061852&_version=1&_urlVersion=0&_userid=7184476&md5=eea57f7c8097bcb0c50f6f9 743f34f58-aff2 Seminars in Immunology, Volume 20, Issue 2, April 2008, pages 86-100, Innate and Adaptive Immune Responses in Tissue Engineering).

Approaches are currently known which are directed to extending the service life of implanted sensor systems. Thus, for example, there are sensor systems which have a plurality of independent sensors configured in a sensor array, and the individual sensors are enabled over time in a coordinated manner during operation of the sensor system. Thus, in this approach, the encapsulation is not directly prevented; instead, after encapsulation of a first sensor of the sensor system occurs, another sensor which is not encapsulated is simply placed in operation. One problem with this approach is that due to their nature, these sensor systems must have a relatively large and complex design since they must accommodate multiple sensors for sequential operation. Besides the space requirements, this also results in significant additional costs.

Alternatively, coatings have been proposed which are designed to selectively suppress or interfere with certain biochemical processes of the agglomeration reactions and processes. However, these coatings usually interact with only one specific step or a few selected steps of the encapsulation process. Since encapsulation may occur via different or alternative processes or process steps, the extent of the influence which is achieved is usually limited. However, encapsulation generally occurs after an initial delay, thus limiting the service life of the sensor system.

The present invention is directed at overcoming one or more of the above-identified problems.

SUMMARY

An object of the present invention is to reduce or prevent one or more disadvantages of the prior art. In particular, it is an object of the present invention to provide an alternative approach which is able to delay or prevent premature encapsulation of an implanted sensor system.

This object is achieved by providing an implantable sensor system comprising a sensor which is situated in a housing, the housing having a measurement region which is permeable for the parameters to be detected by the sensor, characterized in that the measurement region has an erodible protective coating which is permeable for the parameters to be detected by the sensor. The erodible protective coating is preferably applied at least to the side of the measurement region facing away from the sensor.

The invention is based on the surprising finding that the deposition of autologous materials, which is necessary for the initiation of an encapsulation reaction, may be reduced or delayed by the fact that the sensor system has an erodible protective coating. From this erodible protective coating, material layers separate from the sensor surface in a controlled manner in defined time periods. As a result, deposits which have already occurred on the surface of the sensor system are detached and removed. The procedure used is thus independent of the various steps and processes of an encapsulation reaction, and results in effective delay or prevention of encapsulation.

The sensor system according to the invention has a sensor. A sensor is understood to mean a technical component which is able to qualitatively, or, in the form of a measured variable, quantitatively, detect certain physical, chemical, or biochemical characteristics or parameters and/or a material composition of the surroundings. The measured variables are usually detected on the basis of physical or chemical effects, and are converted to variables which may be further processed, for example, electrical signals, which may then be transmitted, optionally via further components of the sensor, to a receiver located in the vicinity.

The sensor may, for example, include a coil for telemetric communication. This telemetric communication may be used, for example, to activate, deactivate, regulate, and/or control the sensor system from outside the body of the recipient after implantation, and also to transmit measurement results.

To protect from environmental influences, the sensor is situated in a housing which essentially encloses the sensor. The housing may have a flexible or a rigid design. The housing preferably includes, or is made of, a nonerodible material. A nonerodible material is understood to mean a material which is essentially resistant to the conditions, the environment, and/or the surroundings after implantation of the sensor system, for a period of time which corresponds at least to the planned service life, the measurement period, or the detection period. The nonerodible material is preferably biocompatible and essentially nonbiocorrodible, however, other types of materials may be used. The nonerodible material is preferably a polymeric, a metallic, or a ceramic material, and/or a mixture containing or comprised of multiple such materials which are the same or different, for example, medical grade stainless steel (MP35N), titanium, platinum/iridium alloy, gold, polyurethane, silicone, epoxy resin, liquid crystal polymer ("LCP"), and the like.

To allow contact between the sensor which is present in the housing and the parameters to be detected, which is necessary so that the sensor may carry out its purpose, a measurement region is provided in the housing. The measurement region is characterized in that it is permeable for the parameters to be detected by the sensor. For this purpose, the measurement region may be designed as a cutout or window in the housing through which contact between the sensor and parameters to be detected is possible. The measurement region may also be designed as part of the surface of the housing, which includes or is comprised of a material which is permeable for the parameters to be detected by the sensor, whereas it is nonpermeable for other environmental parameters. Appropriate permeability for the parameters to be determined may also be achieved by the fact that the housing may have a perforated surface, for example, a perforated diaphragm, in the measurement region, with the openings in the perforation preferably being selected in such a way that the parameters to be detected are able to pass through the openings. Examples of preferred materials for such diaphragms in the measurement region include etched gold or stainless steel foils, perforated LCP films, diaphragms made of poly-L-lactide or another representative of polyesters such as, but not limited to, PDLLA, PLGA, P3HB, P4HB, or mixtures or copolymers thereof, parylene (parylene C or other derivatives), preferably in the form of parylene having pinholes, cellulose films such as nitrocellulose, methylcellulose, or carboxymethylcellulose, for example, or polyvinyl alcohol, whereby the film formation may be optimized by means of the molar mass and deacetylation rate.

The housing of the sensor system may likewise be permeable for the parameters to be detected by the sensor.

The measurement region of the sensor system according to the invention has an erodible protective coating at least on the side facing away from the sensor. The erodible protective coating may contain or be comprised of two or more erodible layers, whereby the individual layers of the protective coating may be the same or different. The erodible protective coating is permeable for the parameters to be detected by the sensor. In particular, for this purpose, the erodible protective coating may be designed as a perforated surface or diaphragm. The openings in the perforation are preferably provided and configured in such a way that the erodible protective coating is permeable for the parameters to be detected by the sensor. In one special embodiment, multiple or even all openings in the perforation are filled with a pH-sensitive hydrogel.

In addition to the measurement region, the erodible protective coating may also completely or partially cover the surface of the housing facing away from the sensor. In one preferred embodiment, the erodible protective coating is applied only to the measurement region.

An erodible protective coating is understood to mean a protective coating which is essentially nonresistant to the conditions, the environment, and/or the surroundings after implantation of the sensor system. Erosion refers to disintegration or separation which occurs in layers, in a process which is defined over time. The erodible protective coating is preferably characterized in that at least one layer of the protective coating is essentially disintegrated or separated at the end of the planned service life or the planned measurement or detection period. In another preferred embodiment, the erodible protective coating is essentially completely disintegrated or separated at the end of the planned service life or the planned measurement or detection period.

The erodible protective coating may be mechanically erodible. Mechanical erodibility is understood to mean that after implantation has occurred, the protective coating is mechanically removed at the implantation site, for example, as the result of bodily movements, motions and/or flows of body fluids, or by temperature variations at the implantation site. This is advantageous, for example, when the sensor system according to the invention is intended for implantation in a liquid stream, for example a flowing body fluid such as blood.

The erodible protective coating may be electrically erodible. Electrical erodibility is understood to mean that, after implantation has occurred, the protective coating is removed due to electrical interactions at the implantation site. This is the case, in particular, when the sensor system according to the invention is designed in such a way that the erodible protective coating functions as a sacrificial anode.

The erodible protective coating may be chemically erodible. Chemical erodibility is understood to mean that, after implantation has occurred, the protective coating reacts with the surroundings at the implantation site due to chemical interactions, and is removed.

The erodible protective coating may be biologically erodible. Biological erodibility is understood to mean that, after implantation has occurred, the protective coating reacts with the surroundings at the implantation site due to biological or biochemical interactions, and is removed. Biological erosion includes erosion which is induced or accelerated by contact with cells or cellular components, in particular, enzymes. One particular form of biological erodibility is biocorrodibility. Within the meaning of the invention, "biocorrodible" refers to substances, materials, alloys, and elements for which decomposition/conversion takes place in the physiological environment, so that a molded body comprised of the material is no longer present, or at least is not predominantly present. Artificial plasma as specified under EN ISO 10993-15:2000 for biocorrosion testing (composition: NaCl 6.8 g/L, $CaCl_2$ 0.2 g/L, KCl 0.4 g/L, $MgSO_4$ 0.1 g/L, $NaHCO_3$ 2.2 g/L, $Na_2HPO_4$ 0.126 g/L, $NaH_2PO_4$ 0.026 g/L) is used as test medium for testing the corrosion characteristics of a particular material. For this purpose, a sample of the materials to be tested is kept at 37° C. in a sealed sample container containing a defined quantity of the test medium. The samples are withdrawn at time intervals of a few hours to several months, depending on the anticipated corrosion characteristics, and analyzed in a known manner for signs of corrosion. The artificial plasma according to EN ISO 10993-15:2000 corresponds to a medium that is similar to blood, thus providing an opportunity to reproducibly duplicate a physiological environment within the meaning of the invention. A substance is referred to as biocorrodible, for example, if it has corroded or reacted by more than 50% in the above-referenced test after the planned service life of the sensor system has elapsed.

The erodible protective coating may be erodible as the result of a change in pH. pH dependent erodibility is understood to mean that, after implantation has occurred, the protective coating reacts at the implantation site due to changes in the pH at or on the surface of the erodible protective coating, and is removed.

The erodible protective coating of the sensor system according to the invention preferably includes or is comprised of a biocompatible erodible polymer, hydrogel, metal, or a mixture thereof. Preferred examples for such polymers, hydrogels, and metals include pretreated, granular, or structured poly-L-lactide, parylene, MP35N, gold, platinum/iridium, magnesium alloys, $Fe_3O_4$, hydrogel, polymers based on acrylamide, methacrylamide, dimethylaminoethyl methacrylate, or a derivative of acrylamide, methacrylamide, dimethylaminoethyl methacrylate [3], or poly-N-isopropylacrylamide [2] and poly-N-isopropylacrylamide-co-allylamine, and PNIPAM with poly(p-dioxanone) as the hard segment.

The erodible protective coating particularly preferably includes or is comprised of a biocorrodible material. Examples of a biocorrodible material include biocorrodible polymers and/or biocorrodible metals or alloys, for example, magnesium alloys, iron alloys, and zinc alloys, or biocorrodible polymers such as polyalkylene phosphate.

In one preferred embodiment of the sensor system according to the invention, the erodible protective coating is designed as a sacrificial anode.

For this purpose the sensor system may have a metallic surface which is designed as a cathode. The cathode may, for example, be a biocompatible metal, or contain or be comprised of a biocompatible alloy. The cathode preferably includes or is comprised of a biocompatible precious metal, stainless steel, titanium, gold, platinum, or an alloy containing one or more of these metals. The metallic surface, which is designed as a cathode, may be provided as a component of the housing. In particular, the housing itself, in whole or in part, may be designed as a cathode.

For this purpose, the erodible protective coating contains one or more metallic layers which are designed as a sacrificial anode. To allow functioning as a sacrificial anode, one, multiple, or all metallic layers of the erodible protective coating are comprised of a material which is less noble than the metallic surface of the cathode. This material which is less noble than the cathode is preferably a metal or alloy. These are preferably biocompatible metals or alloys, particularly preferably biocompatible not noble (base) metals or alloys, for example, magnesium, iron, zinc, or the alloys thereof.

The sensor system according to the invention may also have a voltage source which is connected in an electrically conductive manner to the metallic surface which is designed as a cathode, and to one, multiple, or all metallic layers of the erodible protective coating which are designed as a sacrificial anode. The voltage source is preferably designed to be regulatable and/or controllable, particularly preferably regulatable and/or controllable after implantation has occurred. The rate of erosion of the erodible protective coating may thus be influenced in a targeted manner by applying a selected voltage. The rate of erosion of the erodible protective coating may be decreased by applying a cathodic protection current, and may be increased by applying an anodic corrosion current.

Various other objects, aspects and advantages of the present invention can be obtained from a study of the specification, the drawings, and the appended claims.

DETAILED DESCRIPTION

The invention is explained in greater detail below with reference to exemplary embodiments.

Figure 1:
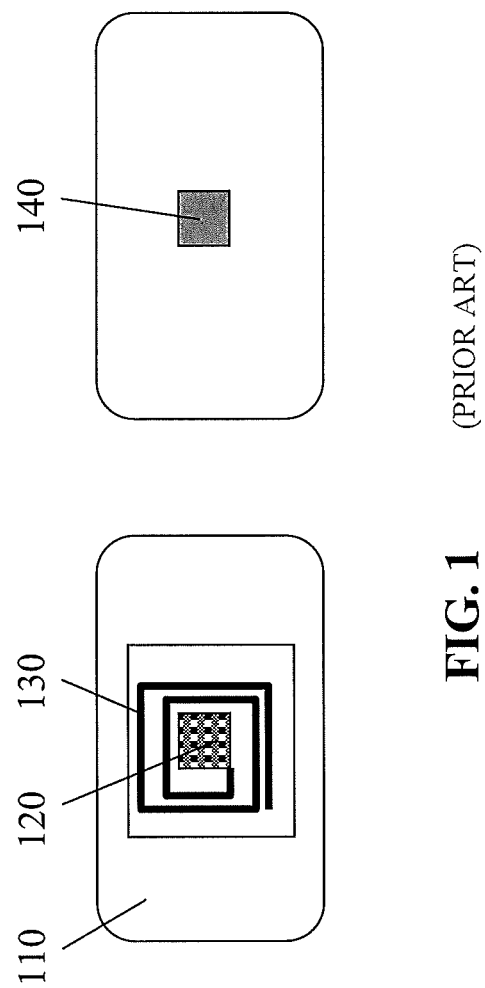
FIG. 1 shows a schematic illustration of a sensor system according to the prior art.

FIG. 1 illustrates a sensor system according to the prior art in order to explain the essential functions and elements of a sensor system. The implantable sensor system is comprised of the actual sensor 120, and optionally a coil 130 for telemetric sensor activation and communication. The sensor 120 and the coil 130 are enclosed by a housing 110 which is comprised of a flexible polymeric material, for example. The housing 110 has a measurement region 140 designed in the form of a cutout. The measurement region 140 is permeable for the parameters to be detected by the sensor 120, and for this purpose allows contact between the actual sensor 120 and the parameters to be detected by the sensor 120.

Starting with the embodiment illustrated in FIG. 1, one arrives at the sensor system according to the invention by providing the measurement region 140 with an erodible protective coating which is permeable for the parameters to be detected by the sensor 120.

Figure 2:
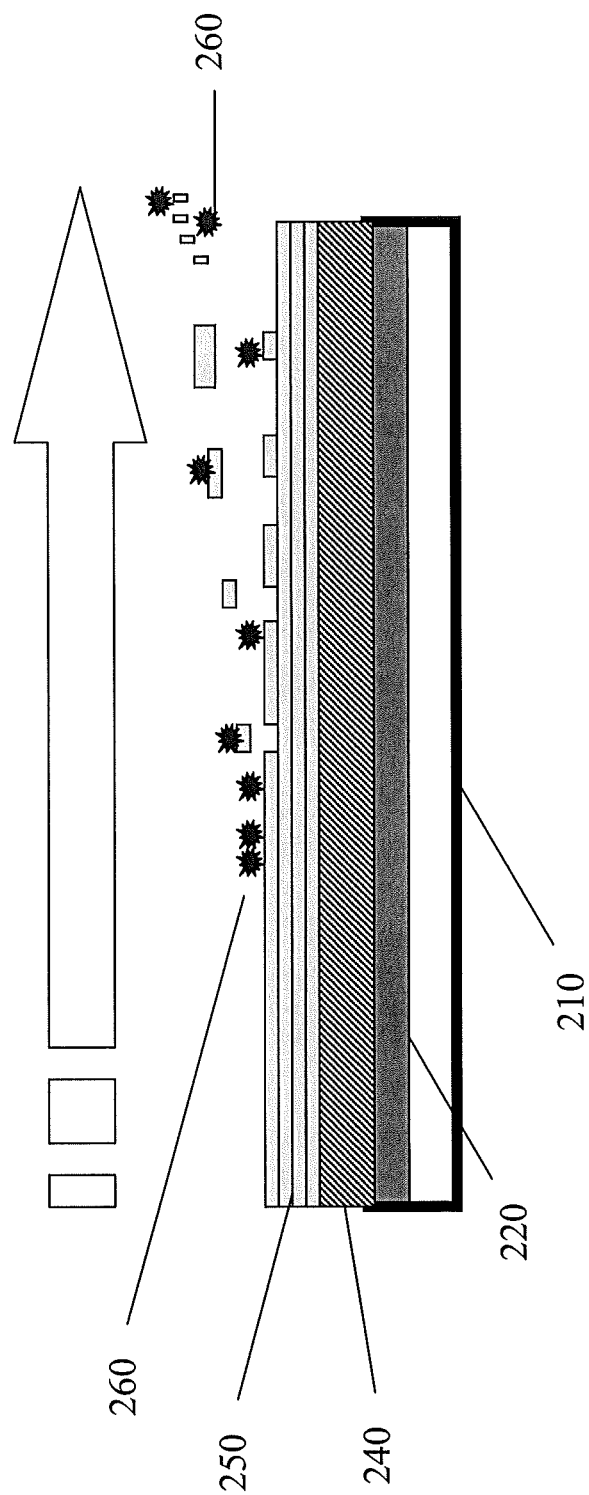
FIG. 2 shows a schematic illustration of a sensor system of a first embodiment of the sensor system according to the invention.

FIG. 2 illustrates a first embodiment of the sensor system according to the invention. The sensor 220 is situated in the housing 210. The measurement region 240 is characterized in that in this region the housing 210 has a cutout which is coated with a nonerodible layer which is permeable for the parameters to be detected by the sensor 220. The measurement region 240 is coated with an erodible protective coating 250, formed from, for example, multiple erodible individual layers, on the side facing away from the sensor 220. If proteins 260, for example, then deposit on the erodible protective coating 250 as an indication of initial encapsulation, the proteins are removed by the time-dependent, progressive erosion (see arrow) of the erodible protective coating 250 before encapsulation of the sensor system can occur. As a result of the erosion of the topmost layer of the erodible protective coating 250, proteins 260 adhering thereto are detached and released. Sensor damage is avoided in this manner.

Figure 3:
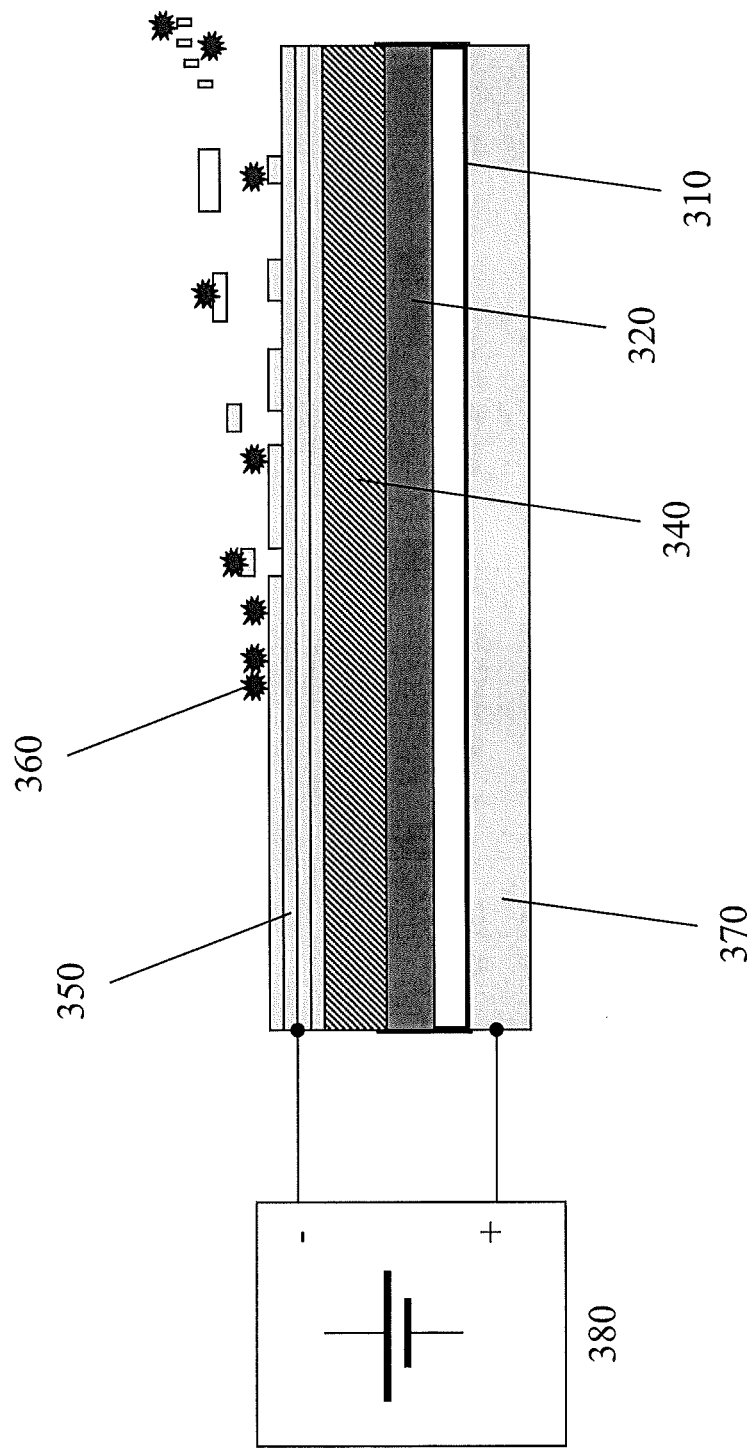
FIG. 3 shows a schematic illustration of a second embodiment of the sensor system according to the invention.

FIG. 3 illustrates a second embodiment of the sensor system according to the invention. The sensor 320 is situated in the housing 310. The measurement region 340 is characterized in that in this region the housing 310 has a cutout which is coated with a nonerodible layer which is permeable for the parameters to be detected by the sensor 320. The measurement region 340 is coated with an erodible protective coating 350, comprised of, for example, multiple erodible individual layers, on the side facing away from the sensor 320. The erodible protective coating 350 is designed as a sacrificial anode. For this purpose, the erodible protective coating 350 may be comprised of one or more metallic layers, whereby the metallic layers preferably contain or are comprised of a biocompatible not noble (base) metal or metal alloy, for example, a magnesium alloy. A metallic surface 370 which is designed as a cathode is provided on the housing 310. The cathode contains or preferably is comprised of a biocompatible metal or metal alloy, and is preferably a precious metal, particularly preferably stainless steel, titanium, gold, or platinum, or alloys containing at least one of these metals. The erodible protective layer 350 as a sacrificial anode, and the metallic surface 370 of the housing 310 as a cathode, are in electrically conductive contact with one another via a regulatable and/or controllable voltage source 380. In FIG. 3, the voltage source 380 is illustrated outside the housing 310 for the sake of clarity. Of course, the voltage source 380 may also be situated on or inside the housing 310. The rate of erosion of the erodible protective coating 350 may be influenced by applying a selected voltage at the voltage source 380. The erosion may thus be speeded up, slowed down, or completely halted for a temporary period of time. The rate of erosion may be controlled, for example, as a function of a sensor calibration signal.

If proteins 360, for example, then deposit on the erodible protective coating 350 as an indication of initial encapsulation, the proteins are removed by regulatable and/or controllable erosion of the erodible protective coating 350 by means of the voltage source 380 before encapsulation of the sensor system can occur. As a result of the erosion of the topmost layer of the erodible protective coating 350, proteins 360 adhering thereto are detached and released. Sensor damage is thus avoided in a regulatable and/or controllable manner.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. An implantable sensor system comprising:
   a sensor which is situated in a housing, the housing having a measurement region which is permeable for parameters detectable by the implantable sensor at an implantation site,
   wherein the measurement region has an erodible protective coating which is permeable for the parameters to be detected by the sensor,
   wherein the erodible protective coating is electrically erodible, wherein portions of the erodible protective coating are removed due to electrical interactions at the implantation site,
   wherein, as the erodible protective coating erodes, protein depositing on the erodible protective coating is carried away to reduce or delay encapsulation, and
   wherein layers of the erodible protective coating separate from a surface of the sensor in a controlled manner in defined time periods.

2. The sensor system according to claim 1, wherein the measurement region is designed as a cutout in the housing.

3. The sensor system according to claim 1, wherein the housing comprises a nonerodible material.

4. The sensor system according to claim 1, wherein the erodible protective coating has two or more erodible layers which are the same.

5. The sensor system according to claim 1, wherein the erodible protective coating comprises an erodible polymer, hydrogel, metal, or a mixture containing one or more of these materials.

6. The sensor system according to claim 1, wherein the erodible protective coating comprises a biocorrodible material.

7. The sensor system according to claim 1, wherein the erodible protective coating is designed as a perforated diaphragm, with openings in the perforation designed and situated in such a way that the erodible protective coating is permeable for the parameters to be detected by the sensor.

8. The sensor system according to claim 7, wherein a plurality or all of the openings in the perforation are filled with a pH-sensitive hydrogel.

9. The sensor system according to claim 1, wherein the erodible protective coating has two or more erodible layers.

10. An implantable sensor system comprising:
    a sensor which is situated in a housing, the housing having a measurement region which is permeable for parameters detectable by the implantable sensor,
    wherein the measurement region has an erodible protective coating which is permeable for the parameters to be detected by the sensor,
    wherein the implantable sensor system includes a metallic surface which is designed as a cathode, and wherein the erodible protective coating comprises at least one metallic layer,
    wherein the at least one metallic layer is designed as a sacrificial anode, wherein the at least one metallic layer of the erodible protective coating comprises an electrically conductive material which is less noble than the metallic surface of the cathode, and wherein portions of the sacrificial anode of the erodible protective coating are removed due to electrical interactions at the implantation site,
    wherein, as the sacrificial anode of the erodible protective coating is removed, protein depositing on the erodible protective coating is carried away to reduce or delay encapsulation, and
    wherein layers of the erodible protective coating separate from a surface of the sensor in a controlled manner in defined time periods.

11. The sensor system according to claim 10, wherein the at least one metallic layer of the erodible protective coating comprises biocompatible base metals or alloys.

12. The sensor system according to claim 10, wherein the metallic surface which is designed as a cathode comprises biocompatible metals or alloys.

13. The sensor system according to claim 10, wherein the metallic surface which is designed as a cathode is a component of the housing.

14. Sensor system according to claim 10, wherein the sensor system further comprises a voltage source which is connected in an electrically conductive manner to the metallic surface which is designed as a cathode, and to one, multiple, or all metallic layers of the erodible protective coating which are designed as a sacrificial anode.

15. The sensor system according to claim 14, wherein the voltage source is regulatable and/or controllable so that the rate of erosion of the erodible protective coating may be influenced in a targeted manner by applying a selected voltage.

* * * * *